US008286491B2

(12) United States Patent
Bourgelas

(10) Patent No.: US 8,286,491 B2
(45) Date of Patent: Oct. 16, 2012

(54) ULTRASONIC INTERNAL ROTATING INSPECTION PROBE THAT SELF-ELIMINATES AIR BUBBLES

(75) Inventor: Tommy Bourgelas, Quebec (CA)

(73) Assignee: Olympus NDT, Waltham, MA (US)

( * ) Notice: Subject to any disclaimer, the term of this patent is extended or adjusted under 35 U.S.C. 154(b) by 304 days.

(21) Appl. No.: 12/621,684

(22) Filed: Nov. 19, 2009

(65) Prior Publication Data

US 2011/0113883 A1    May 19, 2011

(51) Int. Cl.
*G01N 29/04* (2006.01)
(52) U.S. Cl. ............................. 73/623; 73/644
(58) Field of Classification Search ............ 73/623, 73/621, 626, 633, 634, 639, 644
See application file for complete search history.

(56) References Cited

U.S. PATENT DOCUMENTS

| 4,008,603 | A | | 2/1977 | Paulissen |
| 4,149,419 | A | * | 4/1979 | Connell et al. ............ 73/621 |
| 4,212,207 | A | | 7/1980 | Conradi |
| 4,479,388 | A | * | 10/1984 | Matzuk ............ 73/634 |
| 5,046,370 | A | * | 9/1991 | Hall ............ 73/861.89 |
| 5,505,089 | A | * | 4/1996 | Weigel ............ 73/635 |
| 5,529,635 | A | * | 6/1996 | Odell ............ 134/1 |
| 5,531,119 | A | * | 7/1996 | Meyers ............ 73/661 |

* cited by examiner

*Primary Examiner* — J M Saint Surin
(74) *Attorney, Agent, or Firm* — Ostrolenk Faber LLP

(57) ABSTRACT

Disclosed is an improved ultrasonic probe for Internal Rotating Inspection System (called IRIS) for inspecting tube-like structures from the inside of the tubes. The improved design deploys a rotor with rotor blades and a slotted stator located close to the emitting face of the transducer, to direct the flow of water such that air bubbles are carried away from a zone immediately in front of the transducer emitting face. Inspection accuracy and efficiency is significantly improved when air bubbles are effectively removed.

17 Claims, 5 Drawing Sheets

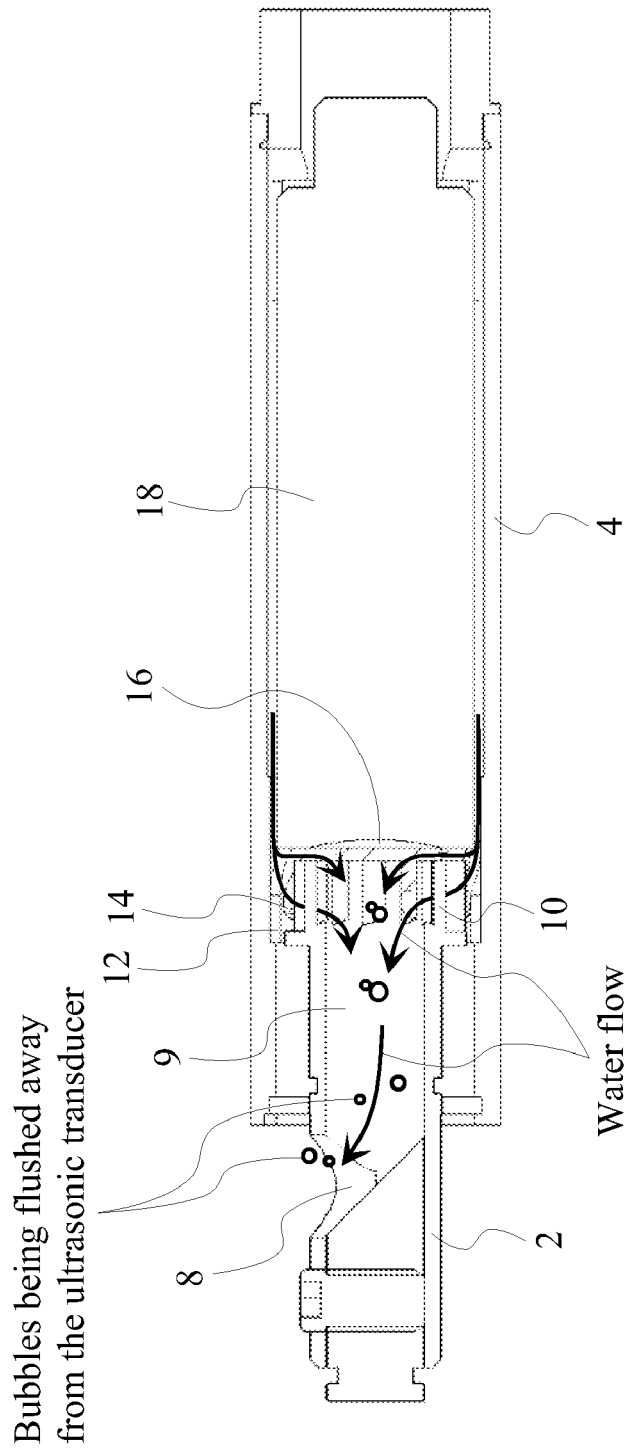

ULTRASONIC INTERNAL ROTATING INSPECTION PROBE THAT SELF-ELIMINATES AIR BUBBLES

FIELD OF THE INVENTION

The present invention relates to non-destructive testing and inspection devices (NDT/NDI) and more particularly to an ultrasonic internal rotating inspection probe assembly that self-eliminates air bubbles in front of the probe sensor.

BACKGROUND OF THE INVENTION

Internal Rotating Inspection System (called IRIS) ultrasonic probes are used to inspect tubes from the inside of the tubes. They measure the thickness and possible defects of the tube wall around the circumference by performing helical scanning as the probe is pulled along the tube's axial direction. An IRIS probe is typically comprised of the following four parts: a) a cable, which brings a coaxial cable for ultrasound measurement signals and pressurized water flow; b) a centering device, which is a mechanically spring-loaded device that centers the probe assembly within the tube to be tested; c) a turbine, which uses the water flow/pressure to propel a rotating 45° mirror that deflects the ultrasonic signal to the tube wall when the tube interior wall is inspected; and d) an ultrasonic transducer that is called an "immersion focalized" transducer that focuses its ultrasonic beam at a small distance in front of its emitting zone. The tube being inspected has to be flooded with water in order for the ultrasonic signals to travel to the tube wall and back again.

IRIS ultrasonic probes as disclosed in U.S. Pat. Nos. 4,008,603 and 4,212,207 are today a common practice for the inspection of in-service tubes such as heat exchanger tubing. These IRIS probes exhibit a significant sensitivity to air bubbles, as the ultrasound waves employed by the device cannot travel through the air. The problem with the current design is that the air bubbles constantly get trapped in front of the ultrasonic transducer, causing an inevitable loss of signal. Eliminating the air bubbles typically requires the operator to shake the probe until the signal is retrieved, which requires not only time of the operator, but experience of the operator in recognizing the presence of the air bubbles. As this is an issue frequently impeding the inspection accuracy and efficiency, it causes significant downtime of the system.

To describe the problem more specifically, reference is made to FIG. 1 showing the existing design of the conventional IRIS probes. The current design of IRIS probes employs an assembly called the "turbine" as it uses pressurized water to propel a reflective mirror P10 which is mounted on a rotor P6. All components are held into a turbine housing P22. The water flow is pushed from the back of the turbine, forced in a thin layer around the ultrasonic transducer P18, and then is deflected by angled slots on a stator P16. The water flow is finally forced into "circumferential jet holes" P12 and exits the mirror hole P8.

As can been seen in FIG. 1, as the water flows in a peripheral layer around stator P16, there is no significant water flow near the immediate front of the transducer ultrasonic coupling face P20. When small air bubbles are present in front face P20, whether coming through the water source or being forced from through the mirror hole P8, they tend to be trapped in front of the transducer ultrasonic coupling face P20, reducing or significantly blocking the ultrasonic waves.

SUMMARY OF THE INVENTION

The invention disclosed herein solves the problems related to the Internal Rotating Inspection System (IRIS) ultrasonic probes, transducers and sensors used in NDT/NDI devices where the existing IRIS probes present the aforementioned drawbacks, such as inaccuracy, loss of signals and undesirable operation down time caused by air bubbles trapped in front of transducers.

Note that the terms "probe", "transducer", and "sensor" used herein may be used interchangeably.

Accordingly, it is a general object of the present disclosure to provide an Internal Rotating Inspection System (IRIS) ultrasonic probe with the capability of self-eliminating undesirable air bubbles to achieve higher inspection accuracy and efficiency.

The increase of water flow for an equivalent pressure of water is a desired condition as it contributes to further elimination of air bubbles and helps further to locally flood the tube under test at the region of the minor hole of the iris.

It is further an object of the present disclosure to provide an improved design of the IRIS probe to achieve less water flow resistance than the conventional IRIS turbine design, therefore resulting in a significant increase of water flow for an equivalent pressure. This in turn further alleviates air-bubble problem through the whole probe and testing area.

It is further an object of the present disclosure to improve the design of the IRIS probe in a manner to help better flood the tube being tested, especially in the region of the mirror hole of the IRIS.

It also can be understood that the presently disclosed probe provides the advantages of better removal of air bubbles in front of the transducers and through-out the probe system and improved water flow with lower resistance.

It can also be understood that the presently disclosed method and probe provide the advantages of higher inspection accuracy, higher operational efficiency less overall operation cost and longer service life.

In addition, it can be appreciated by those skilled in the art that the novel design according to the present disclosure can be employed without any significant increase in manufacturing and operational cost.

BRIEF DESCRIPTION OF THE DRAWINGS

FIG. 2A is cross-sectional view of the preferred embodiment according to the present invention, showing how the new assembly design directs the water flow, flushing air bubbles away from the front of the ultrasonic transducer.

DETAILED DESCRIPTION OF PREFERRED EMBODIMENTS

The preferred embodiment of the present invention proposes a modified IRIS probe turbine that self-eliminates the air bubbles.

The present invention is an improvement to the existing IRIS probe turbine design formed to self-eliminate air bubbles. In the preferred embodiment of the present invention, this is achieved by a modification of the way the water is directed in order to generate the rotation force required to spin the rotor and force the water to flow in front of the ultrasonic transducer.

Figure 1:
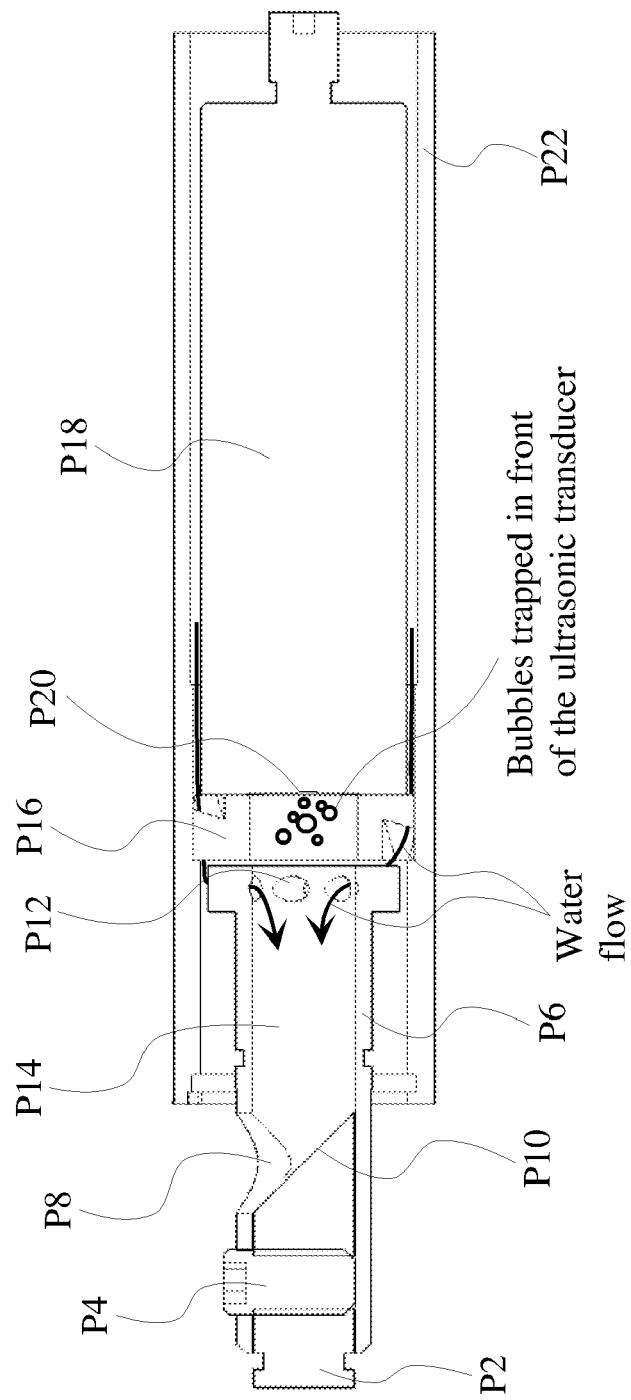
FIG. 1 is a sectional view of a typical prior art IRIS probe turbine, which has the bubble retention problem.
Figure 1A:
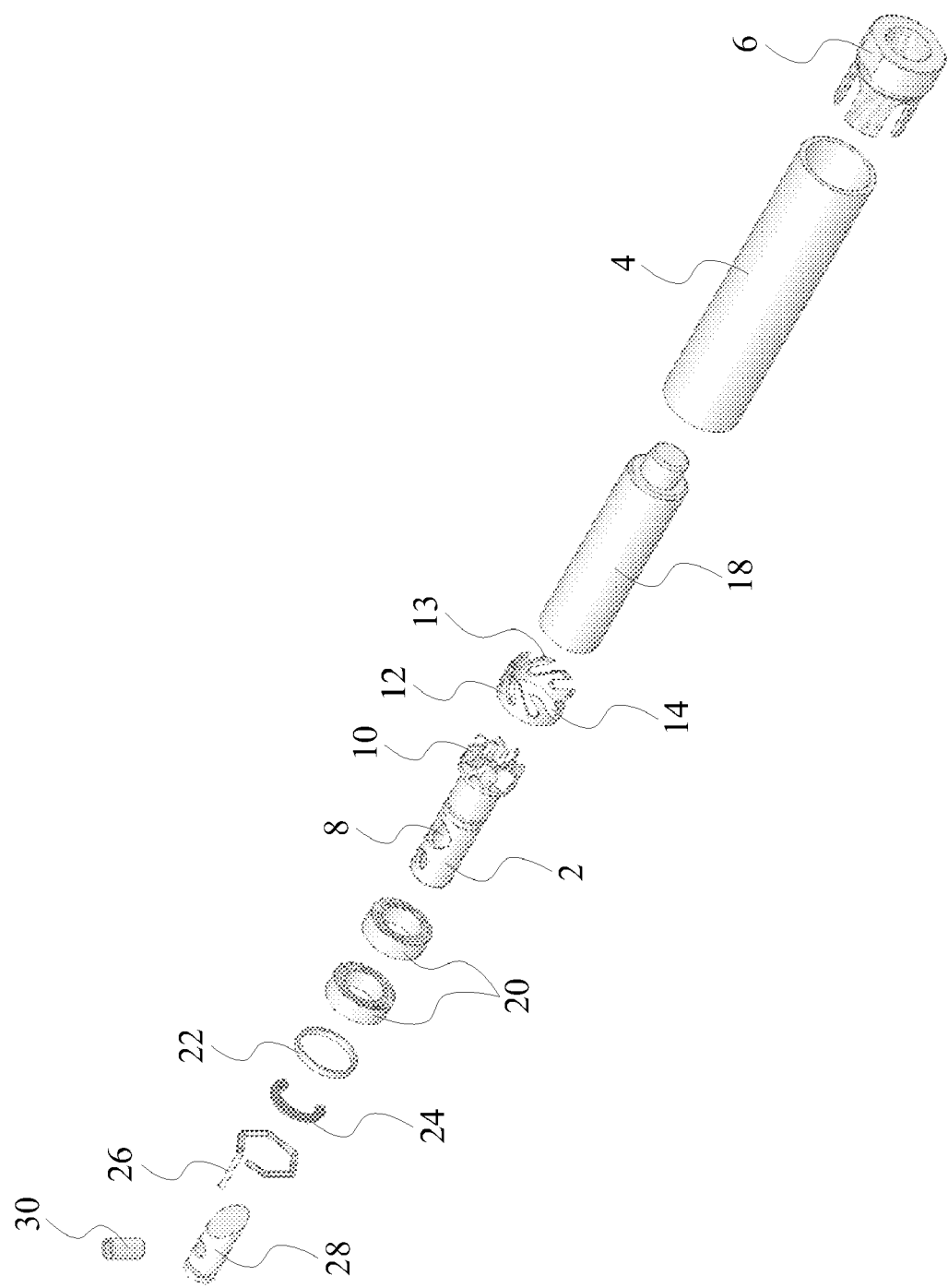
FIG. 1A is an exploded view of the preferred embodiment of the IRIS probe that self-eliminates air bubbles.
Figure 1B:
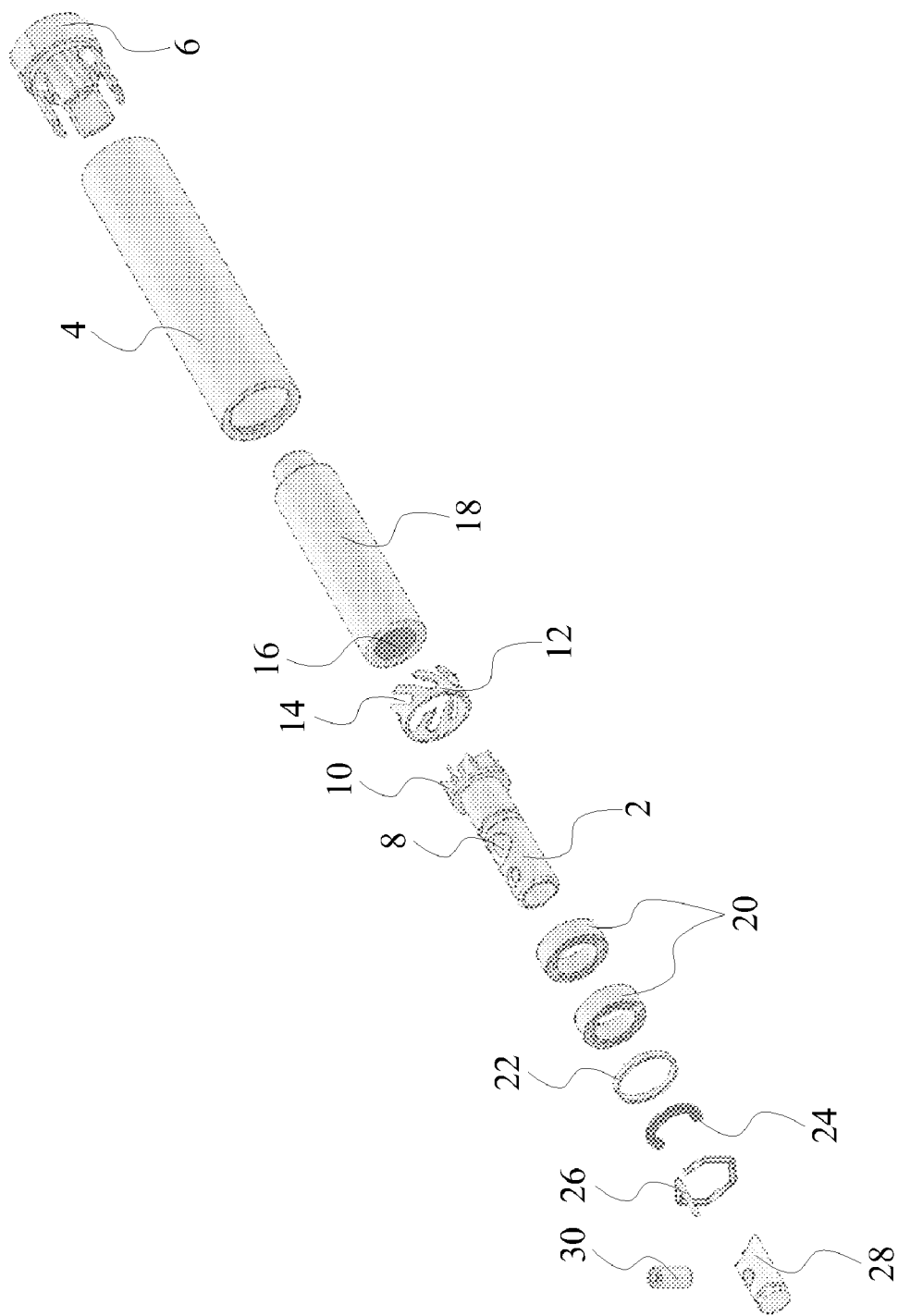
FIG. 1B is another exploded view of the preferred embodiment of the IRIS probe that self-eliminates air bubbles, to show all components from a different angle than FIG. 1A.

Referring now to both FIG. 1A and FIG. 1B, in a preferred embodiment of the present invention, an IRIS probe preferably is comprised of a turbine base 6, turbine housing 4, an ultrasonic transducer 18, a stator 12, a rotor 2 with angled blades 10, two bearings 20, a spacer ring 22, a simple retaining clip 24, a spring pin 26, a rotating acoustically reflective mirror 28 and a simple screw 30. Except for base 6 and transducer 18, all the parts listed here together form an assembly that is normally not disassembled during field operation of the probe.

It should be noted that the assembling manner of all the parts of the herein disclosed probe is exemplary. Variations in assembling manner and use of retaining parts are within the scope of this disclosure when they are employed to achieve the same functionality as described herein.

Continuing with FIGS. 1A and 1B, turbine base 6 is normally assembled on the probe centering device (see background art) transducer 18 is held in place into turbine housing 4 between stator 12 and turbine base 6. The turbine assembly, including housing 4 and rotor 2 are preferably mounted or dismounted on the base 6 in order to change transducer 18.

During an IRIS inspection using the presently disclosed probe, water with predetermined pressure enters from a hose embedded in a co-axial cable (see background art) which is connected to base 6. Water then travels 'up' from base 6 to mirror 28.

Similar to existing methods used in existing IRIS probes, transducer 18 employs piezoelectric material to convert electric pulse to ultrasonic energy, emits and receives ultrasonic pulse energy and converts ultrasonic energy to electric signals.

In the preferred embodiment of the present invention shown in FIGS. 1A and 1B, stator 12 is a separate part that is preferably "press-fitted" within housing 4 in order to fix its position. Stator 12 includes several angled slots 14 that are used to direct the water flow.

Figure 2B:
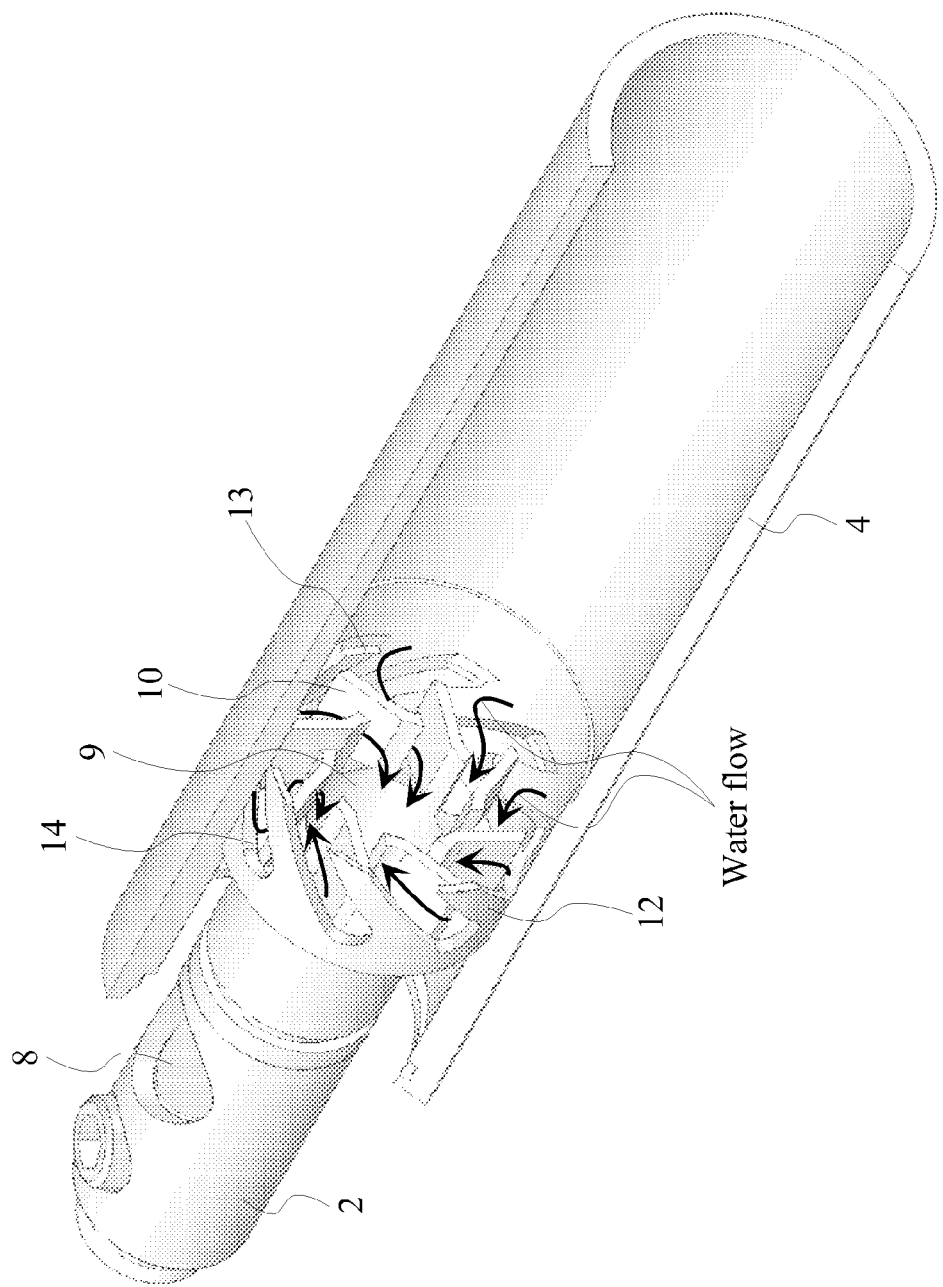
FIG. 2B is another cross-sectional view of the preferred embodiment of the self-eliminating air bubble ultrasonic probe turbine, in order to show the water flow inside the rotor blades.

It should be noted in FIG. 2B that stator 12 also includes a recessed face 13 that prevents the transducer from moving and to come into contact with rotor 2, which is undesirable.

Further continuing with FIGS. 1A and 1B, according to the present invention, rotor 2 is a mobile part that rotates on its axis when the pressured water flowing through turbine blades 10 exerts force upon it. Rotor 2 is centered and allowed to rotate within the inner circumference of bearings 20. Bearings 20 are kept fixed in axial position as they are mounted onto rotor 2 co-axially and confined by spacer ring 22. Part of spacer ring 22 is then held by a synchronization spring pin 26 that is locked into an internal groove at the end of the housing 4. Rotor 2 itself is blocked from moving in the axial position to have direct contact with bearings 20 on the stator side. On the mirror 28 side, simple retaining clip 24 that is fixed on the rotor 2 blocks axial movement of rotor 2 as it is also in contact with the bearings 20.

In the preferred embodiment of the present invention, rotor 2 holds reflective mirror 28 that directs the ultrasonic waves out through the mirror hole 8 and further to the wall of the tube being tested. The test response signal travels this path in the opposite direction. Mirror 28 is simply mounted into rotor 2 preferably with screw 30.

It should be noted that rotor 2 rotates when adequate water flow pressure is applied to angled blades 10.

Reference is now made to FIGS. 2A and 1A. As can be seen in the preferred embodiment of the present invention, the water flow is also forced to form a thin layer around ultrasonic transducer 18, similar to the conventional IRIS probe design. As depicted in FIG. 2B, the water flow is also directed by the stator 12 via angled slots 14.

One important aspect of the novelty herein disclosed, is that these angled slots 14 create a water path flowing to the center of stator 12. As a result, the water flows, passing directly in front of the transducer ultrasonic coupling face 16 (also see FIG. 1B). The transducer ultrasonic coupling face 16 is used to either emit or receive ultrasonic test signals. Allowing water to pass directly in front of face 16 is not presented nor allowed by prior art designs, as the water flow had to pass around the stator rather than within the inner circumferential region where face 16 is located (also see FIG. 1).

As seen in FIG. 1, the space in prior art design between stator rotor P6 and transducer face P20 presents a 'dead' water flow zone with undesirable water flow that traps air bubbles. Another important aspect of the novelties presented in the preferred embodiment of the present disclosure is that stator 12 and rotor blades 10 are mounted to be very close to emitting face 16 of the transducer 18 in FIG. 2A, therefore eliminating the 'dead water flow zone' as shown in existing design within stator P6 in FIG. 1.

Continuing with FIG. 2A and FIG. 2B, in the preferred embodiment of the present invention, the water flow is directed to apply pressure on rotor blades 10 with desirable impact angle to create a spinning motion to rotor 2 on its axis. While most of the water flow is used to propel the rotor 2 as it flows through the blades 10, a lesser part of the water flow is forced to travel in front of transducer ultrasonic coupling face 16. Both parts of water flow continue travel upward through rotor 2, exiting rotor 2 through its center channel 9 and later through mirror hole 8. The travel of the water flow carries away any air bubble that could have been trapped in front of the transducer ultrasonic coupling face 16.

With the preferred embodiment of the current invention, the design of rotor blades 10 offers less resistance to water flow than the original "circumferential jet holes" design (see prior art and FIG. 1), as the blade design offers a much larger "free" section for the water flow than that of the jet holes design.

Important aspects of the present invention involve the design of the rotor 2, especially its blades 10 and stator 12 with its slots 14 that direct the flow of water in a way that the air bubbles are carried away through the rotor hole 9. The other parts of the presently disclosed IRIS probe design remain similar to that of existing designs. The minimum but significant change helps easy adoption of this novel design while providing the significant advantages as follows: 1) it eliminates air bubbles and the problems associated with it; 2) it presents less resistance to water flow than the conventional IRIS turbine design (see prior art & FIG. 1), resulting in a significant increase of water flow for an equivalent pressure. The increase of water flow is a desirable condition as it contributes to further eliminate air bubbles throughout the whole system; and 3) it helps further to locally flood the tube under test in the region near mirror hole 8 where water exits. This feature is particularly useful when inspecting horizontal tubing, which tends to accumulate local air "pockets" around mirror hole 8 that block the transmission of ultrasonic waves. Having more water flow helps to move these air pockets away from the mirror hole 8, resulting in fewer losses of measuring data.

Alternate Embodiments

The following design variations from the preferred embodiment should be recognized by those skilled in the art to be within the scope of the present disclosure. The description of the following alternative embodiments focuses on the portion of the embodiments varied from the preferred embodiment, and should be construed to complement to the preferred embodiment.

One alternative embodiment herein disclosed is to build stator 12 in FIGS. 1A-2B, as part of the turbine housing 4 instead of being machined separately as shown in the preferred embodiment.

Another alternative design is to have rotor blades 14 assembled rather than machined.

Yet another alternative design is to make the shape of rotor blades 10 curved instead of being flat.

Further alternatively, designs can use any number of predetermined rotor blades 10 and stator slots 14.

Yet further, different stator slot and/or rotor blade angles can be employed by alternative designs in order to achieve various rotor speeds.

Although the present invention has been described in relation to particular exemplary embodiments thereof, many other variations and modifications and other uses will become apparent to those skilled in the art. It is preferred, therefore, that the present invention not be limited by the specific disclosure. For example, the scope of the present disclosure may be applied to a wide range of probes such as, but not limited to Ultrasonic (UT) single element, multi-element, and array probes.

What is claimed is:

1. An ultrasonic probe apparatus suitable for inspecting a test object with a hollow longitudinal shape, and with a flowing liquid medium passing through the test object internally during an inspection session, the probe apparatus comprising:
    a transducer having an ultrasonic coupling face and configured to emit ultrasonic pulses and to receive corresponding echo signals;
    an acoustic mirror attached to a rotatable member and configured to guide the ultrasonic pulses and the echo signals between the test object and the transducer;
    a turbine coupled with the rotatable member and configured to be acted upon by the liquid medium to rotate said member and said mirror; and
    liquid channels associated with the turbine and configured to cause the liquid medium to flow through a zone immediately in front of the ultrasonic coupling face, in a manner effective to drive air bubbles away from said zone.

2. The probe apparatus of claim 1, further including a stator, wherein the stator and the rotatable member are mounted in close proximity to the transducer ultrasonic coupling face, and,
    wherein the stator has a plurality of slots configured so that, together with the turbine and rotatable member, it forms the liquid channels guiding the liquid medium to flow through the zone immediately in front of the ultrasonic coupling phase, in a manner effective to drive the air bubbles away from said zone.

3. The probe apparatus of claim 2 wherein the transducer is a single element ultrasonic transducer.

4. The probe apparatus of claim 2, wherein the transducer is a multi-element ultrasonic transducer.

5. The probe apparatus of claim 2, wherein the transducer is a phased array ultrasonic transducer.

6. The probe apparatus of claim 2, wherein the mirror is made from metal material.

7. The probe apparatus of claim 2, wherein the liquid medium is water.

8. The probe apparatus of claim 2, in which the test object is of a tubular shape.

9. The probe apparatus of claim 2, wherein the rotatable member is a rotor.

10. The probe apparatus of claim 2, wherein the turbine further includes a plurality of blades upon which the liquid medium is flown.

11. The probe apparatus of claim 2, wherein the liquid channels comprise at least one a recessed face that prevents the transducer from contacting the rotatable member.

12. The probe apparatus of claim 2, wherein the mirror is attached to the rotatable member by a retaining clip or a screw.

13. The probe apparatus of claim 2, wherein the rotatable member is a rotor, and the liquid channels comprise a stator having slots.

14. The probe apparatus of claim 2, further including a housing for the transducer and the rotatable member.

15. The probe apparatus of claim 14, further including a probe base suited to detachably mount thereto, the rotatable member and the housing, to facilitate repair or replacement of the transducer.

16. The probe apparatus of claim 14, wherein the liquid channels are structured to being press-fitted within the housing.

17. The probe apparatus of claim 14, wherein the housing is machined to form the liquid channels so that the liquid channels are an integral part of the housing.

\* \* \* \* \*